United States Patent
Witzleb et al.

(10) Patent No.: US 10,092,876 B2
(45) Date of Patent: Oct. 9, 2018

(54) RECOVERY OF GASES, ESPECIALLY PERMANENT GASES, FROM STREAMS OF MATTER, ESPECIALLY FROM OFFGAS STREAMS FROM POLYMERIZATIONS

(71) Applicant: LINDE AKTIENGESELLSCHAFT, München (DE)

(72) Inventors: Volker Witzleb, Dresden (DE); Werner Leitmayr, Neuburg/Donau (DE); Christian Voss, Geretsried (DE); Akos Tota, München (DE); Martin Bauer, München (DE)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 15/500,593

(22) PCT Filed: Jul. 23, 2015

(86) PCT No.: PCT/EP2015/001528
§ 371 (c)(1),
(2) Date: Jan. 31, 2017

(87) PCT Pub. No.: WO2016/020042
PCT Pub. Date: Feb. 11, 2016

(65) Prior Publication Data
US 2017/0209830 A1    Jul. 27, 2017

(30) Foreign Application Priority Data

Aug. 7, 2014 (DE) .......................... 10 2014 011 750
Dec. 23, 2014 (EP) ..................................... 14004421

(51) Int. Cl.
*B01D 53/22* (2006.01)
*B01D 53/047* (2006.01)
(Continued)

(52) U.S. Cl.
CPC ......... *B01D 53/229* (2013.01); *B01D 53/047* (2013.01); *C07C 7/005* (2013.01);
(Continued)

(58) Field of Classification Search
CPC ............ B01D 53/229; B01D 2257/102; B01D 2256/24; B01D 53/047; B01D 2257/108
See application file for complete search history.

(56) References Cited

U.S. PATENT DOCUMENTS 4,701,187 A * 10/1987 Choe .................... B01D 53/226
                                                                  95/53
4,750,925 A *  6/1988 MacLean ............... B01D 53/04
                                                                  62/624
(Continued)

FOREIGN PATENT DOCUMENTS

EP           1 024 187 A1    8/2000

*Primary Examiner* — Anthony R Shumate
(74) *Attorney, Agent, or Firm* — Millen White Zelano & Branigan, PC

(57) ABSTRACT

A method of cleaning a stream of matter that includes a C2+ fraction and a first gaseous substance and a second gaseous substance. The stream of matter is subjected to a pressure swing adsorption to remove the C2+ fraction by means of a membrane to obtain a retentate and a permeate. The first substance is enriched in retentate and depleted in permeate and the second substance is depleted in retentate and enriched in permeate.

20 Claims, 1 Drawing Sheet

(51) Int. Cl.
*C07C 7/12* (2006.01)
*C07C 7/144* (2006.01)
*C07C 7/00* (2006.01)

(52) U.S. Cl.
CPC .............. *C07C 7/12* (2013.01); *C07C 7/144* (2013.01); *B01D 2256/24* (2013.01); *B01D 2257/102* (2013.01); *B01D 2257/108* (2013.01); *H05K 999/99* (2013.01)

(56) References Cited

U.S. PATENT DOCUMENTS

| | | | | |
|---|---|---|---|---|
| 5,354,547 | A * | 10/1994 | Rao | B01D 53/22 423/650 |
| 5,411,721 | A * | 5/1995 | Doshi | B01D 53/229 423/220 |
| 5,669,958 | A * | 9/1997 | Baker | B01D 53/002 62/624 |
| 5,856,607 | A * | 1/1999 | Kim | C07C 15/073 585/314 |
| 6,428,606 | B1 | 8/2002 | Gottschlich et al. | |
| 6,592,749 | B1 * | 7/2003 | Lokhandwala | C10G 49/007 208/100 |
| 9,533,254 | B2 * | 1/2017 | McGrath | |
| 2002/0007101 | A1 * | 1/2002 | Senetar | C07C 11/04 585/809 |
| 2003/0033929 | A1 * | 2/2003 | Pinnau | B01D 53/228 95/45 |
| 2003/0073788 | A1 | 4/2003 | Golden et al. | |
| 2004/0099138 | A1 * | 5/2004 | Karode | B01D 3/145 95/214 |
| 2004/0103782 | A1 * | 6/2004 | Wascheck | B01D 53/047 95/50 |
| 2009/0013870 | A1 * | 1/2009 | Sorensen | B01D 53/229 95/96 |
| 2014/0163287 | A1 * | 6/2014 | Keusenkothen | C07C 4/04 585/501 |
| 2015/0122121 | A1 * | 5/2015 | McGrath | B01D 53/228 95/45 |
| 2015/0298972 | A1 | 10/2015 | Ballaguet et al. | |
| 2015/0329439 | A1 * | 11/2015 | Nyce | C10G 50/00 585/259 |
| 2016/0168491 | A1 * | 6/2016 | Yao | C10G 45/00 585/256 |
| 2016/0368834 | A1 * | 12/2016 | Nyce | C10G 50/00 |

* cited by examiner

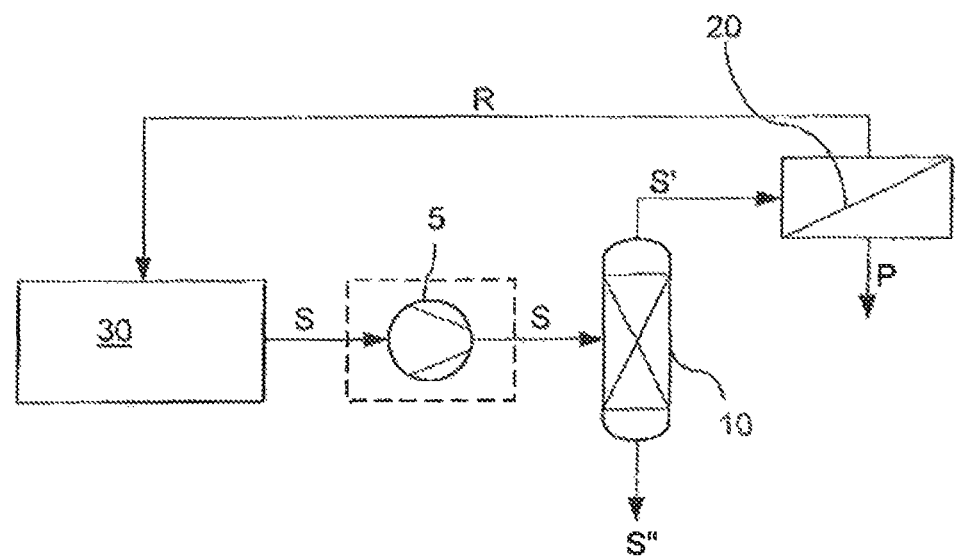

RECOVERY OF GASES, ESPECIALLY PERMANENT GASES, FROM STREAMS OF MATTER, ESPECIALLY FROM OFFGAS STREAMS FROM POLYMERIZATIONS

The invention relates to a method of cleaning a stream of matter, wherein the stream of matter includes a $C_{2+}$ fraction and at least one first gaseous substance and a different second gaseous substance, wherein the stream of matter is subjected to a pressure swing adsorption to remove the $C_{2+}$ fraction.

Cleaning methods of this kind are known from the prior art. For example, EP 1 491 559 describes a method in which an inert gas from an offgas stream of a polymer production plant can be purified by means of an adsorption method and subsequently reused. The polymerization solvent and the monomer are separated here by adsorption from the offgas stream, such that the purified inert gas is at high pressure.

In addition, U.S. Pat. No. 6,706,857 describes a method of recovering olefinic monomers from a polymerization process. In this case, a gas stream composed of monomer and nitrogen is purified by means of pressure swing adsorption.

In the recovery of $C_{2+}$ hydrocarbons (i.e. hydrocarbons having two or more carbon atoms) from streams of matter by means of pressure swing adsorption, what is regularly obtained is a mixture of at least two permanent gas components as high-pressure product, which is frequently subjected merely to thermal utilization by combustion.

Proceeding from this, it is an object of the invention to improve a method of the type specified at the outset to the effect that the use spectrum of the high-gas product is extended.

This problem is solved by a method as described hereinafter.

According to the invention, the stream of matter, after removal of the $C_{2+}$ fraction, is separated by means of a membrane into a retentate and a permeate, the retentate being rich in the first substance, and the permeate by contrast being rich in the second substance. The first substance is thus preferably a substance that permeates less efficiently through the membrane compared to the second substance, such that it is enriched in the retentate, whereas the second substance is depleted in the retentate. Moreover, the second substance permeates better through the membrane compared to the first substance, such that the second substance is enriched in the permeate and the first substance is depleted in the permeate. From a 10/90 $H_2/N_2$ mixture in the feed, it is possible, for example, for $H_2$ to be depleted to less than 1% by volume in the retentate. At the same time, it is possible to achieve hydrogen concentrations above 40% by volume in the permeate.

What is particularly advantageous in the method of the invention is that the retentate is at the same pressure level as the stream of matter that has been cleaned to free it of the $C_{2+}$ fraction and can then be used correspondingly, for example can be recycled into a preceding process—especially without any costly and inconvenient compression. Any pressure drop across the membrane, valves and/or pipelines can be compensated for by a fan. However, this is much less costly and inconvenient compared to the situation where the desired product is on the permeate side.

The first and second substances are preferably gases which, for historic reasons, are also referred to as permanent gases. These are hydrogen, nitrogen, methane, carbon monoxide and carbon dioxide. Preferably, the first substance is nitrogen and the second substance is hydrogen. In addition, the $C_{2+}$ fraction preferably comprises ethylene or propylene.

In addition, the membrane which is used to separate the stream of matter which has been cleaned beforehand to free it of the $C_{2+}$ fraction by pressure swing adsorption preferably includes at least one of the following substances or has been formed from at least one of the following substances: polysulfone (PSU), polyether sulfone (PES), polyimide (PI), polyamide (PA). With membranes of this kind, it is possible, for example, to separate the following pairs of substances: $H_2/N_2$, $H_2/CH_4$ and $N_2/C_{2+}$ ($C_{2+}$ refers to hydrocarbons having two or more carbon atoms).

More preferably, the stream of matter to be cleaned comes from a process conducted upstream of the pressure swing adsorption (for example a method step or method in the form of a synthesis), the stream of matter preferably being an offgas stream from such a process. In this case, the offgas stream may, for example, be a purge gas or a stripping gas.

In one configuration of the method of the invention, the process or method is a polymerization. Such a polymerization in the present context is understood to mean a poly reaction (i.e. polymer formation reaction, called "polymerization" according to IUPAC), i.e. a synthesis reaction which converts identical or different monomers to polymers. The polymerization may especially be what is called a chain polymerization or what is called a staged growth reaction (e.g. polycondensation or polyaddition).

Thus, the stream of matter is preferably an offgas stream, especially a purge gas stream obtained in a polymerization. Monomers used here, for example ethylene or propylene (constituents of the $C_{2+}$ fraction) are then present in the stream of matter or offgas stream which further includes, for example, nitrogen as the first substance (for example when the polymer obtained in the polymerization is purged with nitrogen) and additionally hydrogen as the second substance.

Preferably, after the membrane separation, the retentate is recycled into the process conducted upstream of the pressure swing adsorption and used, for example, to purge a polymer produced or to inertize a polymerization. The permeate (for example containing hydrogen), by contrast, is preferably combusted or optionally sent to another use as export stream.

Further features and advantages of the invention are to be elucidated with reference to the FIGURE in the FIGURE description of a working example which follows. The FIGURE shows:

FIG. 1 a schematic diagram of a working example of a method of the invention

The method of the invention enables separation of a stream of matter S, especially in the form of an offgas stream, consisting of at least two permanent gas components and at least one $C_{2+}$ hydrocarbon. For this purpose, especially after an optional compression 5 of the stream of matter in a first step, the $C_{2+}$ fraction is removed by means of pressure swing adsorption (PSA) 10. The resulting $C_{2+}$-free offgas stream or stream of matter S', which constitutes the high-pressure product of the PSA, is composed of unadsorbed permanent gas components, with at least one component/fraction, for example a first substance, having comparatively poor permeation (and correspondingly becoming enriched in the retentate R) and at least one component/fraction, for example a second substance, having comparatively good permeation through the membrane 20 (and correspondingly becoming enriched in a permeate P). The fraction. S" adsorbed in the pressure swing adsorption is desorbed at lower pressure and optionally sent to a further use. In one example, the PSA is conducted at pressures of 5 bar to 30 bar and at a temperature of 10° C. to 50° C.

By virtue of the inventive addition of a membrane separation 20 downstream of the pressure swing adsorption 10, it is possible to separate the unadsorbed permanent gas components into the retentate R and permeate P and likewise recycle them or utilize them in some other way. In one example, the membrane separation is conducted at a pressure in the range from 5 bar to 30 bar and at a temperature in the range from 20° C. to 80° C.

The special feature here is that the retentate fraction R, in spite of the additional cleaning step, remains at the pressure level of the $C_{2+}$-free offgas stream S' and can be utilized correspondingly.

In one example, in a polymerization process 30, a stream of matter S is obtained in the form of a purge gas stream including nitrogen, hydrogen and a monomer, for example ethylene or propylene.

After the removal of the ethylene or propylene by means of PSA 10, the high-pressure product S' contains only nitrogen and hydrogen. Rather than discarding this gas stream or utilizing it in a purely thermal manner, as has been done to date, the addition of a downstream membrane separation 20 can give a nitrogen-rich retentate R at high pressure and a hydrogen-enriched permeate P at low pressure, with the pressure drop occurring essentially on passage through the membrane 20.

While the hydrogen-rich permeate stream P is still preferably at least partly thermally utilized, the nitrogen/retentate R present at high pressure can be recycled into the polymerization process 30, which can reduce the demand for fresh nitrogen in the polymerization process.

$N_2$ is preferably used to purge the polymer outgassing vessel (POV) or the reactor itself. In particular, $N_2$ is consumed continuously in the POV. The recovery reduces the demand for fresh $N_2$ and reduces the amount flared, which is advantageous in the case of strict environmental regulations.

| List of reference numerals | |
|---|---|
| 5 | Compression |
| 10 | Pressure swing adsorption |
| 20 | Membrane separation |
| 30 | Process, especially polymerization |
| S | Stream of matter or offgas stream |
| S' | Stream of matter cleaned to free it of $C_{2+}$ |
| S" | Adsorbed components (PSA) |
| P | Permeate |
| R | Retentate |

The invention claimed is:

1. A method of cleaning a stream of matter, wherein said stream of matter comprises a $C_{2+}$ fraction, at least one first gaseous substance, and a different second gaseous substance, said method comprising
subjecting said stream of matter to pressure swing adsorption to remove said $C_{2+}$ fraction, and
after removal of the $C_{2+}$ fraction, separating said stream of matter by means of a membrane, wherein said stream of matter is separated into a retentate and a permeate, wherein said at least one first gaseous substance is enriched in the retentate and said second gaseous substance is depleted in the retentate, and said at least one first gaseous substance is depleted in the permeate and said second gaseous substance is enriched in the permeate.

2. The method as claimed in claim 1, wherein the first and second gaseous substances are selected from hydrogen, nitrogen, methane, carbon monoxide and carbon dioxide.

3. The method as claimed in claim 1, wherein said membrane comprises at least one of the following substances: polysulfone, polyether sulfone, polyimide, and polyamide.

4. The method as claimed in claim 1, wherein said stream of matter is an offgas stream.

5. The method as claimed in claim 1, wherein said stream of matter is obtained in a process conducted upstream of the pressure swing adsorption.

6. The method as claimed in claim 5, wherein said retentate is recycled into the process.

7. The method as claimed in claim 5, wherein said process comprises polymerization, and wherein the stream of matter is obtained as an offgas stream of the polymerization.

8. The method as claimed in claim 1, wherein said $C_{2+}$ fraction contains ethylene or propylene.

9. The method as claimed in claim 1, wherein said first gaseous substance is nitrogen.

10. The method as claimed in claim 1, wherein said second gaseous substance is hydrogen.

11. The method as claimed in claim 1, further comprising combusting said permeate.

12. The method as claimed in claim 1, wherein said membrane is formed from at least one of the following substances: polysulfone, polyether sulfone, polyimide, and polyamide.

13. The method as claimed in claim 5, wherein said process comprises polymerization, and wherein the stream of matter is obtained as an offgas stream of said polymerization by purging a polymer produced by said polymerization with a gas stream.

14. The method as claimed in claim 9, wherein said second gaseous substance is hydrogen.

15. The method as claimed in claim 8, wherein said first gaseous substance is nitrogen and said second gaseous substance is hydrogen.

16. The method as claimed in claim 1, wherein
said stream of matter is obtained from a polymerization process, conducted upstream of the pressure swing adsorption, wherein ethylene or propylene is used as monomer in said polymerization process,
wherein said $C_{2+}$ fraction contains ethylene or propylene, said first gaseous substance is nitrogen, and said second gaseous substance is hydrogen, and
wherein said retentate is recycled to said polymerization process.

17. The method as claimed in claim 16, wherein said retentate is used to purging a polymer produced by said polymerization.

18. The method as claimed in claim 16, wherein said stream of matter is a purge gas or a stripping gas obtained from said process.

19. The method as claimed in claim 1, wherein said pressure swing adsorption is conducted at pressures of 5 bar to 30 bar and at a temperature of 10° C. to 50° C.

20. The method as claimed in claim 1, wherein said separating by said membrane is conducted at a pressure in the range from 5 bar to 30 bar and at a temperature in the range from 20° C. to 80° C.

* * * * *